(12) United States Patent
Rule et al.

(10) Patent No.: US 10,918,537 B2
(45) Date of Patent: Feb. 16, 2021

(54) ABSORBENT ARTICLE COMPRISING FLEXIBLE POLYMERIC FOAM AND INTERMEDIATES

(71) Applicant: 3M INNOVATIVE PROPERTIES COMPANY, St. Paul, MN (US)

(72) Inventors: Joseph D. Rule, Woodbury, MN (US); Delton R. Thompson, Jr., Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 372 days.

(21) Appl. No.: 15/760,092

(22) PCT Filed: Oct. 3, 2016

(86) PCT No.: PCT/US2016/055103
§ 371 (c)(1),
(2) Date: Mar. 14, 2018

(87) PCT Pub. No.: WO2017/062294
PCT Pub. Date: Apr. 13, 2017

(65) Prior Publication Data
US 2018/0250176 A1 Sep. 6, 2018

Related U.S. Application Data

(60) Provisional application No. 62/237,195, filed on Oct. 5, 2015.

(51) Int. Cl.
*A61F 13/534* (2006.01)
*C08G 18/48* (2006.01)
(Continued)

(52) U.S. Cl.
CPC ......... *A61F 13/534* (2013.01); *A61F 13/535* (2013.01); *A61L 15/425* (2013.01);
(Continued)

(58) Field of Classification Search
CPC .............................. A61F 2013/530649; A61F 2013/530802–530861; A61F 13/00021;
(Continued)

(56) References Cited

U.S. PATENT DOCUMENTS 2,957,207 A 10/1960 Roop
RE24,906 E 12/1960 Ulrich
(Continued)

FOREIGN PATENT DOCUMENTS

EP 0453286 10/1991
EP 1078616 2/2001
(Continued)

OTHER PUBLICATIONS

"What is foam compression set?" https://www.stockwell.com/blog/what-is-foam-compression-set/, Sep. 3, 2015 (Year: 2015).*
(Continued)

*Primary Examiner* — Susan S Su
(74) *Attorney, Agent, or Firm* — Carolyn A. Fischer

(57) ABSTRACT

Absorbent articles are described comprising a first absorbent layer comprising a polymeric foam. In one embodiment, the polyurethane foam comprises the reaction product of a polymeric polyisocyanate component having an equivalent weight of no greater than 250 g/equivalent; and a polyol component. The polyol component comprises one or more polyether polyols such that the polyol component comprises an average equivalent weight ranging from 500 to 2000 g/equivalent; an ethylene oxide content ranging from 15-30 wt.-%; a secondary hydroxyl content of at least 55 wt.-% and less than 80 wt.-% of the total hydroxyl content of the polyol component; and less than 5 wt-% water. Also described are various composites comprising the polyurethane foam described herein in combination with another substrate such
(Continued)

as a second absorbent layer, a fluid impervious backsheet, and/or a fluid pervious topsheet.

23 Claims, 1 Drawing Sheet

(51) Int. Cl.
| | |
|---|---|
| C08G 18/76 | (2006.01) |
| A61L 15/42 | (2006.01) |
| A61F 13/535 | (2006.01) |
| C08G 18/20 | (2006.01) |
| C08G 18/18 | (2006.01) |
| C08L 75/04 | (2006.01) |
| A61F 13/53 | (2006.01) |
| C08G 101/00 | (2006.01) |

(52) U.S. Cl.
CPC ......... *C08G 18/18* (2013.01); *C08G 18/1808* (2013.01); *C08G 18/2081* (2013.01); *C08G 18/4816* (2013.01); *C08G 18/4837* (2013.01); *C08G 18/4841* (2013.01); *C08G 18/7671* (2013.01); *C08L 75/04* (2013.01); *A61F 2013/530649* (2013.01); *C08G 2101/005* (2013.01); *C08G 2101/0083* (2013.01); *C08G 2220/00* (2013.01)

(58) Field of Classification Search
CPC .................. A61F 13/534; A61F 13/535; A61F 2013/15121; A61F 2013/15146; A61F 2013/530343; A61F 2013/5307; A61L 15/425
See application file for complete search history.

(56) References Cited

U.S. PATENT DOCUMENTS

| | | | |
|---|---|---|---|
| 3,900,030 A | 8/1975 | Bashan | |
| 4,394,930 A | 7/1983 | Korpman | |
| 4,410,571 A | 10/1983 | Korpman | |
| 4,610,678 A | 9/1986 | Weisman | |
| 4,673,402 A | 6/1987 | Weisman | |
| 5,147,345 A | 9/1992 | Young | |
| 5,201,727 A | 4/1993 | Nakanishi | |
| 5,229,427 A | 7/1993 | Madaj | |
| 5,250,581 A | 10/1993 | Gastinger | |
| 5,352,711 A * | 10/1994 | DesMarais | A61F 13/53 |
| | | | 521/149 |
| 5,387,207 A | 2/1995 | Dyer | |
| 5,472,437 A | 12/1995 | Akiyama | |
| 5,489,620 A | 2/1996 | Bleys | |
| 5,601,542 A | 2/1997 | Melius | |
| 5,730,739 A | 3/1998 | Lavash | |
| 5,763,335 A | 6/1998 | Hermann | |
| 5,853,402 A | 12/1998 | Faulks | |
| 5,900,437 A * | 5/1999 | Mitchell | C08J 9/28 |
| | | | 521/62 |
| 5,948,829 A | 9/1999 | Wallajapet | |
| 6,033,769 A | 3/2000 | Brueggemann | |
| 6,034,149 A | 3/2000 | Bleys | |
| 6,107,356 A | 8/2000 | DesMarais | |
| 6,107,538 A | 8/2000 | Young | |
| 6,156,951 A | 12/2000 | Gustafsson | |
| 6,174,929 B1 | 1/2001 | Hahnle | |
| 6,271,277 B1 | 8/2001 | Bleys | |
| 6,406,648 B1 | 6/2002 | Noel | |
| 6,417,241 B1 | 7/2002 | Huygens | |
| 6,486,378 B1 | 11/2002 | Areskoug | |
| 6,506,959 B2 | 1/2003 | Hamajima | |
| 6,515,195 B1 | 2/2003 | Lariviere | |
| 6,551,295 B1 | 4/2003 | Schmidt | |
| 6,570,057 B1 | 5/2003 | Schmidt | |
| 6,586,502 B2 | 7/2003 | Wallace | |
| 6,620,493 B2 | 9/2003 | Hasegawa | |
| 6,685,682 B1 | 2/2004 | Heinecke | |
| 6,689,934 B2 | 2/2004 | Dodge, II | |
| 6,723,892 B1 | 4/2004 | Daley | |
| 6,852,905 B2 | 2/2005 | Baker | |
| 6,855,739 B2 | 2/2005 | Becker | |
| 6,881,875 B2 | 4/2005 | Swenson | |
| 6,896,669 B2 | 5/2005 | Krautkramer | |
| 6,977,323 B1 | 12/2005 | Swenson | |
| 6,989,005 B1 * | 1/2006 | LaVon | A61F 13/51498 |
| | | | 604/385.14 |
| 7,189,768 B2 | 3/2007 | Baran, Jr. | |
| 7,329,715 B2 | 2/2008 | Wang | |
| 7,781,525 B2 | 8/2010 | Yano | |
| 8,318,823 B2 | 11/2012 | Triouleyre | |
| 2002/0090453 A1 | 7/2002 | Muthiah | |
| 2002/0143308 A1 * | 10/2002 | Reeves | C08L 39/06 |
| | | | 604/377 |
| 2005/0250866 A1 * | 11/2005 | Champ | A61L 15/18 |
| | | | 521/99 |
| 2006/0030632 A1 | 2/2006 | Krueger | |
| 2006/0148907 A1 | 7/2006 | Nicholson | |
| 2007/0014947 A1 | 1/2007 | Mengel | |
| 2007/0179210 A1 | 8/2007 | Swaniker | |
| 2009/0118387 A1 * | 5/2009 | Sakakibara | C08G 18/4833 |
| | | | 521/170 |
| 2010/0228209 A1 | 9/2010 | Carlucci | |
| 2011/0110996 A1 | 5/2011 | Schoenberger | |
| 2012/0053547 A1 | 3/2012 | Schroeder | |
| 2012/0078154 A1 | 3/2012 | Pigg | |
| 2012/0175556 A1 | 7/2012 | Rudolf | |
| 2013/0171393 A1 | 7/2013 | Kannankeril | |
| 2013/0274349 A1 | 10/2013 | Qin | |
| 2014/0295134 A1 * | 10/2014 | Wood | B32B 5/18 |
| | | | 428/135 |
| 2015/0080823 A1 | 3/2015 | Thompson | |
| 2015/0119837 A1 | 4/2015 | Thompson, Jr. | |
| 2015/0374561 A1 * | 12/2015 | Hubbard, Jr. | A61L 15/22 |
| | | | 604/369 |
| 2015/0374876 A1 * | 12/2015 | Hubbard, Jr. | B01J 20/28054 |
| | | | 502/402 |
| 2016/0317354 A1 * | 11/2016 | Weisman | A61F 13/00068 |

FOREIGN PATENT DOCUMENTS

| | | |
|---|---|---|
| JP | 3060095 | 7/2000 |
| JP | 2003-509161 | 3/2003 |
| JP | 3789470 | 6/2006 |
| JP | 4794266 | 10/2011 |
| WO | WO 1993-04092 | 3/1993 |
| WO | WO 1994-13704 | 6/1994 |
| WO | WO 1996-23024 | 8/1996 |
| WO | WO 2008/036173 | 3/2008 |
| WO | WO 2011/045147 | 4/2011 |
| WO | WO 2013-180832 | 12/2013 |
| WO | WO 2013-180937 | 12/2013 |
| WO | WO 2013-188083 | 12/2013 |

OTHER PUBLICATIONS

"How are polyols characterized?" The Dow Chemical Company, printed Jun. 6, 2020 (Year: 2020).*
"3M™ Tegaderm™ High Performance Foam Adhesive Dressing", Brochure, 2010, pp. 1-8.
"Adhesives, Coatings and Elastomers, Isocyanate Product Line 2010", Huntsman, 2010, pp. 1-2.
"ARCOL® E-434, Polyether Polyol", Bayer Material Science, Product Information, pp. 1.
"CARPOL® GP-700 Polyether Polyol", Technical Data Sheet, CAS No. 25791-96-2, Carpenter Co., Chemicals Division, 2011, pp. 1-2.
"Dabco® BA100 Blocking Agent", Polyurethane Additives Product Bulletin, Air Products, 2011, pp. 1-2.
"DOW Specialty Amines, TEA Fast Facts", Ethanolamine—TEA, Dow Chemical Company, 2012, 1 page.
"LiquiBlock™ HS Fines", Technical Data, Emerging Technologies Inc., 1 page.

(56) References Cited

OTHER PUBLICATIONS

"Polyether Polyol, CDB-33142", Technical Data Sheet, Chemicals Division, Carpenter Co., 2012, pp. 1-2.
"Rigid Foam High Density Molded", Dabco® Air Products, 2012, 1 page.
"Rubinate® 1245 MDI, Modified Polymeric Diphenylmethane Diisocyanate", Technical Data Sheet, Huntsman, 2010, pp. 1-3.
"Rubinate®/Suprasec® MDI Specialty Isocyanates", Huntsman, pp. 1-2.
Forrest, "Chemical Characterization of Polyurethanes", 1999, pp. 3-13.
Ludewig, "Allophanate Structures as Building Blocks for Very Low Viscous Urethane Acrylates", RadTech Europe 2005 Conference & Exhibition, 2005, pp. 1-6.
Lundquist, "MCS-533: 5/32 Polycril 400 Foam on Liner", CS-05-000533, 3M, 2009, pp. 1-12.
Randall "The Polyurethanes Book", 2013, URL <https //web archive org/web/20130611142855/http://www essentialchemicalindustry.org/polymers/polyurethane html>, pp. 1-52.
Skok, "New Modified Liquid Pure MDI for Case Applications", Huntsman Polyurethanes, pp. 1-9.
Thirumal, "Effect of Foam Density on the Properties of Water Blown Rigid Polyurethane Foam", Journal of Applied Polymer Science, 2008, vol. 108, No. 03, pp. 1810-1817.
International Search Report for PCT International Application No. PCT/US2016/055103, dated Jan. 31, 2017, 6 pages.

\* cited by examiner

ABSORBENT ARTICLE COMPRISING FLEXIBLE POLYMERIC FOAM AND INTERMEDIATES

CROSS REFERENCE TO RELATED APPLICATIONS

This application is a national stage filing under 35 U.S.C. 371 of PCT/US2016/055103, filed Oct. 3, 2016, which claims the benefit of U.S. Provisional Application No. 62/237,195, filed Oct. 5, 2015, the disclosure of which is incorporated by reference in its/their entirety herein.

BACKGROUND OF THE INVENTION

In the field of disposable absorbent articles, "superabsorbent polymers" (SAP) mixed with cellulose fibers provides a good means for storing aqueous fluids. However, such material has also been described as not enhancing fluid transport. When a phenomena often referred to as "gel-blocking" takes place, a reduction in fluid transport can occur.

Thus, many absorbent core designs have been described comprising components or layers with separate functionality, i.e. a liquid storage material and also a different material that provides acquisition and distribution of the fluid ("ADL").

Open celled polymeric foams have been described for use in disposable absorbent articles. One type of foam that has been described is made from high internal phase emulsions (also referred to as "HIPE"). Polyurethane foams have also been described for use in disposable absorbent articles.

SUMMARY

Although various absorbent articles have been described, industry would find advantage in alternative absorbent articles, particularly those having improved properties.

In one embodiment an absorbent article is described comprising a first absorbent layer comprising a polymeric foam having an average cell size of at least 100 microns, a density of less than 3 lbs/ft$^3$, and a gel content greater than 90%. The polymeric foam has at least one property selected from a) an indentation force at 65% deflection of less than 5 kPa; or b) a constant deflection compression set of less than 25%; or a combination of a) and b); and a second absorbent layer in fluid communication with the first absorbent layer.

In another embodiment, an absorbent article is described comprising a first absorbent layer comprising a polyurethane foam comprising the reaction product of a polymeric polyisocyanate component having an equivalent weight of no greater than 250 g/equivalent; and a polyol component. The polyol component comprises one or more polyether polyols such that the polyol component comprises an average equivalent weight ranging from 500 to 2000 g/equivalent; an ethylene oxide content ranging from 15-30 wt.-%; a secondary hydroxyl content of at least 55 wt.-% and less than 80 wt.-% of the total hydroxyl content of the polyol component; and less than 5 wt-% water. The absorbent article further comprises a second absorbent layer in fluid communication with the first absorbent layer.

Also described are polyurethane foam compositions and various composites comprising the polyurethane foam described herein in combination with another substrate such as a second absorbent layer, a fluid impervious backsheet, and/or a fluid pervious topsheet.

DETAILED DESCRIPTION

Figure 1:
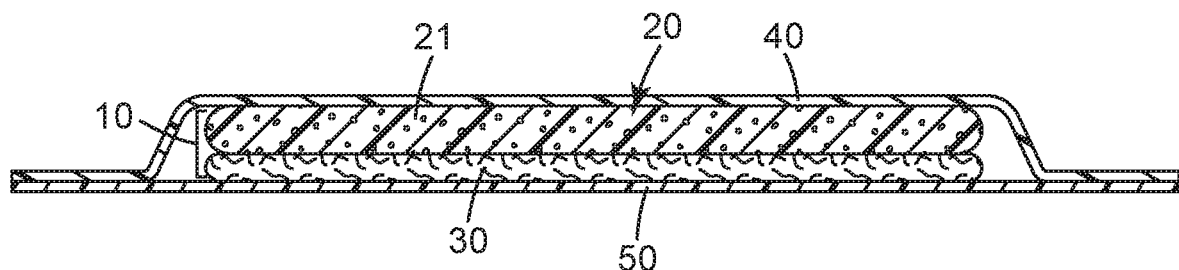
FIGS. 1-4 are cross-sectional views of absorbent articles comprising an absorbent composite, the absorbent composite having various arrangements of first and second absorbent layers.

With reference to FIG. 1, a cross-sectional view of an absorbent article comprising an absorbent composite 10 disposed between a fluid pervious topsheet 40 and fluid impervious backsheet 50. The absorbent composite comprises a first absorbent layer 20 and a second absorbent layer 30 in fluid communication with each other. The first absorbent layer comprises a polymeric foam 21. The layers are sufficiently proximate (i.e. near to) each other such that fluid from the first layer is readily transported to the second layer. In some embodiments, the first and second layers are in direct contact with each other. In other embodiments, one or more additional layers are disposed between the first and second layer. Such additional layer or layers do not detract from the intended properties of the absorbent composite (e.g. such as absorption capacity, strike-through, and rewet). In one embodiment, a tissue layer is disposed between the first and second absorbent layers. Favored absorbent articles include feminine hygiene articles, disposable diapers, and adult incontinence articles.

In a favored embodiment, the first absorbent layer functions as and thus will be referred to as a "fluid transport layer". Fluid transport layers quickly absorb the liquid through the absorbent article's top sheet for temporary retention (e.g., to act as a temporary reservoir), and to transfer that liquid into the underlying second absorbent layer at a rate at which the second absorbent layer can absorb for final or permanent retention. The fluid transport typically improves "wicking" of the absorbent article by spreading the body fluid in the "x" and "y" plane over the area of the second absorbent layer covered by the fluid transport layer while also carrying the fluid in the "z" direction to the second absorbent layer.

The absorbent composite comprises a first absorbent layer comprising a polymeric foam material. The polymeric foam comprises a continuous phase of a hydrophilic polymer. By "continuous" it is meant that the cell structure is substantially continuous, lacking discernible boundaries within the cell structure. In contrast, a layer formed from foam particles would be characterized as comprising a discontinuous layer since a plurality of discrete boundaries would be evident between neighboring foam particles. The foam of the absorbent composite optionally comprises discrete pieces of superabsorbent polymer dispersed within the polymeric foam. When present, the discrete pieces of superabsorbent polymer are typically uniformly distributed within the polymeric foam.

The polymeric foams described herein are predominantly open-celled. This means the individual cells of the foam are in complete, unobstructed communication with adjoining cells. The cells in such substantially open-celled foam structures have intercellular openings or "windows" that are large enough to permit fluid transfer from one cell to the other within the foam structure. The individual cells may be defined by a plurality of mutually connected, three dimensionally branched webs. The strands of polymeric material making up these branched webs can be referred to as "struts." A foam material is typically "open-celled" if at least 80% of the cells in the foam structure that are at least 1 micrometer in size are in fluid communication with at least one adjacent cell. Thus, a portion of the cells (up to 20%) of the foam may be closed. The minimum cell size is typically at least 5, 10, 15, 20, 25, or 30 micrometers.

In addition to being open-celled, the polymeric foams are sufficiently hydrophilic to permit the foam to absorb aqueous fluids. The internal surfaces of the foam structures can be rendered hydrophilic by the selection of (e.g. hydrophilic) components during the formation of the polymeric foam or by post-treatment.

The average cell size of the total foam structure is typically at least 100 microns. In some embodiments, the average cell size is at least 150, 200, 250, or 300 microns. The average cell is typically no greater than 1000, 900, 800, or 700 microns. In some embodiments, the average cell size may be no greater than 650 microns or 600 microns. As used herein, average cell size refers to the average cell size as determined using a microscope, as further described in the examples.

In some embodiments, the foam has a relatively uniform cell size. For example, the average cell size on one major surface may be about the same or vary by no greater than 10% as compared to the opposing major surface. In other embodiments, the average cell size of one major surface of the foam may differ from the opposing surface. For example, in the foaming of a thermosetting material it is not uncommon for a portion of the cells at the bottom of the cell structure to collapse resulting in a lower average cell size on one surface. When the foam has a gradient of average cell size, it is preferred that the surface having the smaller average cell size is in fluid communication with the second (e.g. fluid storage) absorbent layer.

The foam is typically a non-collapsed foam. A non-collapsed foam typically does not substantially expand upon contact with aqueous fluids, such as body fluids.

In favored embodiments, the foam of the (e.g. fluid transport) first absorbent layer is a polyurethane foam. Polyurethane polymers are generally formed by the reaction of at least one polyisocyanate component and at least one polyol component. The polyisocyanate component may comprise one or more polyisocyanates. The polyol component may comprise one or more polyols. The concentration of a polyol may be expressed with regard to the total polyol component. The concentration of polyol or polyisocyanate may alternatively be expressed with regard to the total polyurethane concentration.

Various aliphatic and aromatic polyisocyanates have been described in the art. The polyisocyanate utilized for forming the polyurethane foam typically has a functionality between from 2 and 3. In some embodiments, the functionality is no greater than about 2.5.

In one embodiment, the foam is prepared from at least one aromatic polyisocyanate. Examples of aromatic polyisocyanates include those having a single aromatic ring such as are toluene 2,4 and 2,6-diisocyanate (TDI) and naphthalene 1,5-diisocyanate; as well as those having at least two aromatic rings such as diphenylmethane 4,4'-, 2,4'- and 2,2'-diisocyanate (MDI).

In favored embodiments, the foam is prepared from one or more (e.g. aromatic) polymeric polyisocyanates. Polymeric polyisocyanates typically have a (weight or number average) molecular weight greater than a monomeric polyisocyanate (lacking repeating units), yet lower than a polyurethane prepolymer. Thus, the polyurethane foam is derived from at least one polymeric polyisocyanate that lacks urethane linkages. In other words, the polyurethane foam is derived from a polymeric isocyanate that is not a polyurethane prepolymer. Polymeric polyisocyanates comprises other linking groups between repeat units, such as isocyanurate groups, biuret groups, carbodiimide groups, uretonimine groups, uretdione groups, etc. as known in the art.

Some polymeric polyisocyanates may be referred to as "modified monomeric isocyanate". For example pure 4,4'-methylene diphenyl diisocyanate (MDI) is a solid having a melting point of 38° C. and an equivalent weight of 125 g/equivalent (or in other words 125 g per isocyanate group). However, modified MDIs, are liquid at 38° C. and have a higher equivalent weight (e.g. 143 g/equivalent). The difference in melting point and equivalent weight is believed to be a result of a small degree of polymerization, such as by the inclusion of linking groups, as described above.

Polymeric polyisocyanates, including modified monomeric isocyanate, may comprise a mixture of monomer in combination with polymeric species inclusive of oligomeric species. For example, polymeric MDI is reported to contain 25-80% monomeric 4,4'-methylene diphenyl diisocyanate as well as oligomers containing 3-6 rings and other minor isomers, such as 2,2' isomer. In some embodiments, the polymeric isocyanate has an average functionality of at least 2 (2.0-2.2).

Polymeric polyisocyanates typically have a low viscosity as compared to prepolymers. The polymeric isocyanates utilized herein typically have a viscosity no greater than about 300 cps at 25° C. and in some embodiments no greater than 200 cps or 100 cps at 25° C. The viscosity is typically at least about 10, 15, 20 or 25 cps at 25° C.

The equivalent weight of polymeric polyisocyanates is also typically lower than that of prepolymers. The polymeric isocyanates utilized herein typically have an equivalent weight of no greater than about 250 g/equivalent and in some embodiments no greater than 200 g/equivalent or 175 g/equivalent. In some embodiments, the equivalent weight is at least 130 g/equivalent.

In some embodiments, the polyurethane is derived from a single polymeric isocyanate or a blend of polymeric isocyanates. Thus, 100% of the isocyanate component is polymeric isocyanate(s). In other embodiments, a major portion of the isocyanate component is a single polymeric isocyanate or a blend of polymeric isocyanates. In these embodiments, at least 50, 60, 70, 75, 80, 85, 90, 95 or greater wt.-% of the isocyanate component is polymeric isocyanate(s). In typical embodiments, the polymeric polyisocyanate is present in an amount ranging from 30 to 45 wt.-% of the total polyurethane foam.

Some illustrative polyisocyanates include for example, polymeric MDI diisocyanate from Huntsman Chemical Company, The Woodlands, Tex., under the trade designation "RUBINATE 1245"; and modified MDI isocyanate available from Huntsman Chemical Company under the trade designations "SUPRASEC 9561" or "SUPRASEC 9634".

The aforementioned isocyanates are reacted with a polyol to prepare the polyurethane foam material. The polyurethane foams are hydrophilic, such that the foam absorbs aqueous liquids, particularly body fluids. The hydrophilicity of the polyurethane foams is typically provided by use of an isocyanate-reactive component, such as a polyether polyol, having a high ethylene oxide content. Examples of useful polyols include adducts [e.g., polyethylene oxide, polypropylene oxide, and poly(ethylene oxide-propylene oxide) copolymer] of dihydric or trihydric alcohols (e.g., ethylene glycol, propylene glycol, glycerol, hexanetriol, and triethanolamine) and alkylene oxides (e.g., ethylene oxide, propylene oxide, and butylene oxide). Polyols having a high ethylene oxide content can also be made by other techniques as known in the art. Suitable polyols typically have an average functionality of 2 to 3.

The polyurethane foam is typically derived from (or in other words is the reaction product of) at least one polyether polyol having ethylene oxide (e.g. repeat) units. The polyether polyol typically has an ethylene oxide content of at least 5, 10, 15, 20 or 25 wt-% and typically no greater than 75 wt-%. Such polyether polyol has a higher functionality than the polyisocyanate. In some embodiments, the average functionality is about 3. The polyether polyol typically has a viscosity of no greater than 1000 cps at 25° C. and in some embodiments no greater than 900, 800, or 700 cps. The molecular weight (Mn) of the polyether polyol is typically at least 500 or 1000 g/mole and in some embodiments no greater than 6000, or 5000 g/mole. Illustrative polyols includes for example a polyether polyol product obtained from the Carpenter Company, Richmond, Va. under the designations "CARPOL GP3008", "CARPOL GP4520", "CARPOL GP-5171", and "CARPOL GP-725".

In typical embodiment, at least two, three or four polyether polyols are utilized in amounts to provide the average equivalent weight and ethylene oxide content just described.

In some embodiments, one or more polyether polyols having a high ethylene oxide content and a molecular weight (Mn) of no greater than 5500, or 5000, or 4500, or 4000, or 3500, or 3000 g/mole, as just described, are the primary or sole polyether polyols of the polyurethane foam. For example, such polyether polyols constitute at least 50, 60, 70, 80, 90, 95 or 100 wt-% of the total polyol component. Thus, the polyurethane foam may comprise at least 25, 30, 35, 40, 45 or 50 wt-% of polymerized units derived from such polyether polyols.

In other embodiments, one or more polyether polyols having a high ethylene oxide content are utilized in combination with other polyols. In some embodiments, the other polyols constitute at least 1, 2, 3, 4, or 5 wt-% of the total polyol component. The concentration of such other polyols typically does not exceed 20, or 15 wt-% of the total polyurethane. Illustrative other polyols include a polyether polyol product (Chemical Abstracts Number 25791-96-2) that can be obtained from the Carpenter Company, Richmond, Va. under the designations "CARPOL GP-1000", "CARPOL GP-700, and CARPOL GP-3000". In some embodiments, such optional other polyols may comprise polypropylene (e.g. repeat) units.

The polyol component typically comprises one or more polyether polyols such that the polyol component has an average equivalent weight ranging of at least 500, 550, 600, 650, 700, 750, or 800 g/equivalent ranging up to 2000 g/equivalent. In some embodiments, the polyol component has an average equivalent weight of no greater than 1900, 1800, 1700, 1600, 1500, 1400, or 1300 g/unit.

The polyol component typically comprises one or more polyether polyols such that the polyurethane foam generally has an ethylene oxide content of at least 15, 15.5, 16, 16.5 or 17 wt-% and no greater than 30, 29, 28 or 27 wt-%. In some embodiments, the polyurethane foam has an ethylene oxide content of no greater than 26, 25, 24, 23, 22, 21, or 20 wt-%. When the ethylene oxide content is too low, the foam can be undesirably hard as reflected by the indentation force deflection and constant deflection compression set values. In addition, when the ethylene oxide content is too low, the foam can have undesirably poor water absorption properties.

The polyol component typically comprises one or more polyether polyols such that the secondary hydroxyl content of the polyol component is at least 55 or 60 mole % ranging up to 80 mole % of the total hydroxyl content of the polyol component with the exception of water. In some favored embodiments, secondary hydroxyl content of the polyol component is greater than 61 mole % and less than 80, 79, 78, or 77 mole %. When the secondary hydroxyl content is too low, the foam can be undesirably hard as reflected by the indentation force deflection and constant deflection compression set values. In addition, when the secondary hydroxyl content is too low, a shrinking foam can result. When the secondary hydroxyl content is too high, the foam can collapse.

The average equivalent weight, ethylene oxide content, and secondary hydroxyl content of the polyol component can be calculated as described in further detail in the forthcoming examples.

The kinds and amounts of polyisocyanate and polyol components are selected such that the polyurethane foam is relatively soft, yet resilient. These properties can be characterized for example by indentation force deflection and constant deflection compression set, as measured according to the test methods described in the examples. In some embodiments, the polyurethane foam has an indentation at 65% deflection of less than 5, 4.5, 4, 3.5, 3, or 2.5 kPa. In some embodiments, the indentation force deflection at 25% or 65% is typically at least 0.5, 0.75, 1, or 1.25 kPa. In some embodiments, the polyurethane foam has an indentation force at 25% deflection of less than 2 kPa. The constant deflection compression set at 50% deflection can be zero and is typically at least 0.5, 1 or 2% and generally no greater than 35%. In some embodiments, the constant deflection compression set at 50% deflection is no greater than 30%, or 25%, or 20%, or 15%, or 10%.

The polyurethane foam may comprise known and customary polyurethane formation catalysts such as organic tin compounds and/or an amine-type catalyst. The catalysts are preferably used in an amount of from 0.01 to 5 wt-% of the polyurethane. The amine-type catalyst is typically a tertiary amine. Examples of suitable tertiary amine include monoamines such as triethylamine, and dimethyl cyclohexylamine; diamines such as 1,4-diazabicyclo(2,2,2)octane, tetramethylethylenediamine, and tetramethylhexanediamine; triamines such as tetramethylguanidine; cyclic amines such as triethylenediamine, dimethylpiperadine, and methylmorphorine; alcoholamines such as dimethylaminoethanol, trimethylaminoethylethanolamine, and hydroxyethylmorphorine; ether amines such as bisdimethylaminoethyl ethanol; diazabicycloalkenes such as 1,8-diazabicyclo (5,4,0) undec-7-ene (DBU), and 1,5-diazabicyclo(4,3,0)nonene-5; and organic acid salts of the diazabicycloalkenes such as phenol salt, 2-ethylhexanoate and formate of DBU. These amines can be used either singly or in combination. The amine-type catalyst can be used in an amount no greater than 4, 3, 2, 1 or 0.5 wt-% of the polyurethane.

The polyurethane typically comprises a surfactant to stabilize the foam. Various surfactants have been described in the art. In one embodiment a silicone surfactant is employed that comprises ethylene oxide (e.g. repeat) units, optionally in combination with propylene oxide (e.g. repeat) units such as commercially available from Air Products under the trade designation "DABCO DC-198". In some embodiments, the concentration of hydrophilic surfactant is at least 0.075 or 0.1 ranging up to 1 or 2 wt-% of the polyurethane. When the surfactant concentration is insufficient, the saline absorption rate can be slow (e.g. greater than 100, 200, or 300 seconds).

The polyurethane foam may comprise various additives such as surface active substances, foam stabilizers, cell regulators, blocking agents to delay catalytic reactions, fire retardants, chain extenders, crosslinking agents, external and internal mold release agents, fillers, pigments (titanium dioxide), colorants, optical brighteners, antioxidants, stabilizers, hydrolysis inhibitors, as well as anti-fungal and anti-bacteria substances. Such other additives are typically collectively utilized at concentrations ranging from 0.05 to 10 wt-% of the polyurethane.

In some embodiments, the absorbent foam is white in color. Certain hindered amine stabilizers can contribute to discoloration, such as yellowing, of the absorbent foam. In some embodiments, the absorbent foam is free of diphenylamine stabilizer and/or phenothiazine stabilizer.

In other embodiments, the absorbent foam may be a colored (i.e. a color other than white). The white or colored absorbent foam can include a pigment in at least one of the components. In preferred embodiments, pigment is combined with a polyol carrier and is added to the polyol liquid stream during manufacture of the polyurethane foam. Commercially available pigments include for example DispersiTech™ 2226 White, DispersiTech™ 2401 Violet, DispersiTech™ 2425 Blue, DispersiTech™ 2660 Yellow, and DispersiTech™ 28000 Red from Milliken in Spartansburg, S.C. and Pdi® 34-68020 Orange from Ferro in Cleveland, Ohio.

In the production of polyurethane foams, the polyisocyanate component and polyol component are reacted such that an equivalence ratio of isocyanate groups to the sum of hydroxyl groups is no greater than 1 to 1. In some embodiments, the components are reacted such that there are excess hydroxyl groups (e.g. excess polyol). In such embodiments, the equivalence ratio of isocyanate groups to the sum of the hydroxy groups is at least 0.8:1. In some embodiments, the equivalence ratio or in other words index is at least 0.85:1, or 0.9:1, or 0.95:1, or 1:1.

The gel content of the polyurethane is typically at least 80 or 85% and preferably ranging from 90, 91 or 92% to 100%.

Polyurethane foams can be prepared by mixing the reactants in liquid form with a suitable amount of water or chemical blowing agent, suitable catalyst and other optional components, and allowing the mixture to foam and set. It is preferred to use water for producing the polyurethane foams, because the water reacts with the isocyanate groups to liberate carbon dioxide. The amount of water is preferably in the range from 0.5 to 5% wt-% polyurethane. In some embodiments, the amount of water is no greater than 4 or 3.5 or 3 or 2.5 or 2 wt.-% of the (prepolymerized) polyurethane.

Polyurethane foam can be made by various methods as described in the art. In the preparation of polyurethanes, two or more liquid streams are usually combined. The mixing of such liquid streams initiates polymerization and the foaming of the polymerizing material. The foams can be prepared by any known processing methods. In some cases, polymerization and shaping are effected in one step, for example, casting the foam into a continuous thin layer appropriate for an absorbent article. In some cases, polyurethanes are prepared in the form of slabstock, which is subsequently cut to the desired shape. The slabstock can be prepared in either a batch process or a continuous process. In some cases, the polyurethane can be polymerized in a cylindrical shape which is then peeled to make a long, thin layer of foam. In some cases, the polyurethane can be polymerized in a long, generally rectangular shape that is subsequently cut into thinner foam layers appropriate for use in an absorbent article. In some cases, several thin layers of foam can be spliced to form a single, longer layer that may facilitate manufacturing of absorbent articles. In most cases, the liquid streams are a polyisocyanate component (often referred to as "component A") and a polyol component (often referred to "component B"). Mixing of component A and component B can be accomplished in either high or low pressure delivery systems. Usually component B will contain water which reacts with the polyisocyanate of component A to form an amine and to release $CO_2$, which in turn functions as a blowing gas. In some cases, auxiliary blowing agents, such as inert gases $CO_2$ or $N_2$, or high vapor pressure solvents, or chemical blowing agents such as azo and diazo compounds, may be incorporated. Such methods are well described in the literature (See for example "Polymeric Foams and Foam Technology; Daniel Klempner & Vahid Sendijarevic").

In one embodiment, the polyurethane foams are generally prepared by continuous casting of a thin layer of foam onto a substrate, such as described in U.S. Pat. No. 2,957,207. Although U.S. Pat. No. 2,957,207 emphasizes the importance of introducing a limited delay after the polyol component and polyisocyanate component have been mixed, such delay is not typically utilized when the foam is conveyed between a pair of metering rolls such that the gap setting of the metering rolls controls the thickness of the foam. The foam is typically cured at an over temperature ranging from about 100° F. to 275° F. Alternatively the foam can be made as blocks that are cut to the desired thickness or by casting the foam in an open or closed metallic mold.

The (e.g. polyurethane) polymeric foam of the first absorbent (e.g. fluid transport) layer may optionally comprise a superabsorbent polymer (SAP), also referred to as "hydrogels" and "hydrocolloids", such as described in patent application Ser. No. 61/652,408, filed May 29, 2012. The SAP is substantially water-insoluble, but water-swellable polymers capable of absorbing large quantities of liquids (e.g. 10-100 times their weight). Various SAP materials have been described in the art. (See for example U.S. Pat. Nos. 4,410,571; 6,271,277; and 6,570,057; incorporated herein by reference.) These include superabsorbents with low gel strength, high gel strength, surface cross-linked superabsorbents, uniformly cross-linked superabsorbents, or superabsorbents with varied cross-link density throughout the structure. Superabsorbents may be based on chemistries that include poly(acrylic acid), poly(iso-butylene-co-maleic anhydride), poly(ethylene oxide), carboxy-methyl cellulose, poly(-vinyl pyrrolidone), and poly(-vinyl alcohol). The superabsorbents may range in swelling rate from slow to fast. The superabsorbents may be in various degrees of neutralization. Counter-ions are typically Li, Na, K, Ca.

Favored SAP materials can be slightly network cross-linked polymers of partially neutralized polyacrylic acids or starch derivatives thereof. For example, the SAP may comprise from about 50 to about 95%, preferably about 75%, neutralized, slightly network crosslinked, polyacrylic acid (i.e. poly (sodium acrylate/acrylic acid)). As described in the art, network crosslinking serves to render the polymer substantially water-insoluble and, in part, determines the absorptive capacity and extractable polymer content characteristics of the precursor particles and the resultant macrostructures.

For embodiments wherein the foam comprises SAP, the SAP is generally present within the foam as discrete pieces. Such pieces may have various shapes such as spherical, rounded, angular, or irregular pieces as well as fibers. The particles generally comprise a distribution of sizes ranging from about 1 micron to 500 microns in diameter or cross-section (largest dimension when not spherical). The particles are preferably a finely divided powder of a maximum particle size of less than 400, 300, or 200 microns.

When present, the concentration of SAP in the polymeric foam is typically at least 1, 2, 3, 4, or 5 wt-% of the (e.g. polyurethane) polymeric composition and typically no greater than 30, 25, or 20 wt-% of the (e.g. polyurethane) polymeric composition. The minimal amount of SAP that can provide the desired properties (e.g. absorption capability, strike-through, rewet) is utilized. In some embodiments, the concentration of SAP is no greater than 17.5, or 15, or 12.5 or 10 wt-% of the (e.g. polyurethane) polymeric composition. In some embodiments, the inclusion of the SAP in the foam has little or no effect on the absorption capacity of the foam, yet surprisingly improves the strikes through and rewet of the foam and especially the absorbent composite.

The SAP particles can be incorporated into the polymeric foam by mixing the SAP with the ingredients used for making foam. In the direct addition of the SAP during the production of the (e.g. polyurethane) polymeric foams, the SAP is typically added to the polyol component. However, other methods for incorporating the SAP into the polymeric foams have also been described, such as described in U.S. Pat. No. 6,271,277.

For embodiments wherein the foam comprises SAP, the SAP is typically uniformly distributed within the polymeric material of the first absorbent layer. However, the first absorbent layer may comprise more than one layer, wherein the layers have a different concentration of SAP. For example, a polymeric foam layer having a lower concentration of SAP may be proximate the topsheet and a polymeric foam layer having a higher concentration may be proximate the second absorbent layer.

The hydrophilic (e.g. polyol(s)) component(s) of the (e.g. polyurethane) polymeric foam provide the desired absorption capacity of the foam. Thus the foam may be free of superabsorbent polymer. Further, the polyurethane foam is free of amine or imine complexing agent such as ethylenimine, polyethylenimine, polyvinylamine, carboxy-methylated polyethylenimines, phosphono-methylated polyethylenimines, quaternized polyethylenimines and/or dithiocarbamitized polyethylenimines; as described for example in U.S. Pat. Nos. 6,852,905 and 6,855,739.

The average density of the (e.g. polyurethane) polymeric foam is typically at least 1.8, 2.0, or 2.2 and no greater than 3 lbs/ft$^3$.

The (i.e. uncompressed) thickness of the foam-containing first absorbent (e.g. fluid transport) layer is at least 0.1 millimeters and typically no greater than about 10 millimeters. In some embodiments, the thickness is between about 1 millimeters and about 5 millimeters. A skilled artisan will appreciate that the preferred thickness may vary depending on the particular size of absorbent garment, and its intended use. For example, for larger babies and adults, a higher absorption capacity material typically is needed.

The first and second absorbent layers and absorbent composite can have various shapes including symmetrical (having a point, line, or plane of symmetry) or unsymmetrical shapes. Shapes that are envisioned include but are not limited to circles, ovals, squares, rectangles, pentagons, hexagons, octagons, trapezoids, truncated pyramids, hourglasses, dumbbells, dog bones, etc. The edges and corners can be straight or rounded. The sides can be curved (convex or concave), tapered, flared, or angled. In some embodiments, the absorbent composite has an hour-glass or trapezoid shape.

The second absorbent layer can have the same size and shape as the first absorbent layer. In this embodiment, substantially an entire major surface of the first absorbent layer (e.g. polymeric foam) is in contact with or in fluid communication with the second absorbent layer. Alternatively, the second absorbent layer can have a different size and/or shape than the first absorbent layer. In some embodiments, the second absorbent layer has a length and/or width that is less than the length and/or width of the first absorbent layer (e.g. polymeric foam). Thus, a portion of the first absorbent layer (e.g. polymeric foam) is not in contact with or in fluid communication with the second absorbent layer. Typically the second absorbent layer is arranged such that it is in contact with or in fluid communication with the central region of the first absorbent layer (e.g. polymeric foam). Thus, when the second absorbent layer has a length and/or width that is less than the first absorbent layer (e.g. polymeric foam), opposing perimeter regions or the entire perimeter region of the first absorbent layer (e.g. polymeric foam) is not in contact with or in fluid communication with the second absorbent layer. In some embodiments, the surface area of the major surface of the second absorbent layer that faces and is fluid communication with the first absorbent layer (e.g. polymeric foam) ranges from about one/half to three/fourths (e.g. about two/thirds) of the total surface area of the major surface of the first absorbent layer (e.g. polymeric foam) facing the second absorbent layer. In one embodiment, the first absorbent layer (e.g. polymeric foam) has an hour-glass shape and the second absorbent layer is a rectangular strip spanning the central longitudinal axis of the hour-glass, the rectangular strip having a width slightly less than the narrowest (middle) portion of the hour-glass.

The foam can contain cut-out regions that create voids, cavities, depressions, channels, or grooves. In one embodiment, at least the central region of the foam comprises a plurality of circular perforations having a diameter of about 1 mm, spaced about 3 mm apart.

The first and/or second absorbent layers and/or the absorbent composite may comprise various functional additives including for example, antimicrobial coatings, ion capturing coatings, desiccants, fragrance, and odor control particles.

Regardless of the shape, the first and second absorbent layers and absorbent composite can generally be defined as having a first major face, an opposing second major face substantially parallel to the first major face, and a thickness in a direction orthogonal to the first and opposing major face.

In some favored embodiments, the first absorbent layer functions as a fluid transport layer and the second absorbent layer functions as the fluid storage layer. Other layers, such as a tissue layer, may be disposed between the first absorbent (e.g. fluid transport) layer and second absorbent (e.g. fluid storage) layer. The presence of these other layers do not detract from and typically have little effect on the properties of the absorbent composite. In such embodiments, the second absorbent layer has at least the same and typically a higher absorption capacity than the first absorbent layer. For example, the second absorbent layer typically has an average absorption capacity of at least 20, 21, 22, 23, 24 g/g or at least about 25-30 g/g (i.e. at least 25, 26, 27, 28, 29, or 30 g/g) or at least 8 g/cc. In some embodiments, the second absorbent layer has an average absorption capacity of no greater than 60 or 55 or 50 or 45 or 40 g/g. The first absorbent layer has an average absorption capacity of at least 5, 6, 7, 8, 9, or 10 g/g; yet typically less than 20 or 15 g/g.

The second absorbent material can be made of a variety of materials. In some embodiments, the second absorbent material is the same or similar (e.g. polyurethane) polymeric foam having more SAP than the first absorbent layer. In another embodiment, the second absorbent layer comprises fibrous materials, typically in the form of a fibrous web.

Although the fluid transport layer and fluid storage layer are both absorbent, the fluid storage layer has a considerably greater absorption capacity than the fluid transport layer. In one embodiment, the absorption capacity (g/g or g/cc) of the second layer is at least 1.5×, 2×, 2.5×, or even 3× the absorption capacity of the first absorbent layer (i.e. ×). In some embodiments, the absorption capacity of the second layer is typically no greater than 5× or 4.5× or 4×.

The fibers of the second (e.g. fluid storage) layer are hydrophilic, or can be a combination of both hydrophilic and hydrophobic fibers. Suitable fibers include those that are naturally occurring fibers (modified or unmodified), as well as synthetically made fibers. Examples of suitable unmodified/modified naturally occurring fibers include cotton, Esparto grass, bagasse, hemp, flax, silk, wool, wood pulp, chemically modified wood pulp, jute, rayon, ethyl cellulose, and cellulose acetate.

Suitable wood pulp fibers can be obtained from known chemical processes such as, but not limited to the Kraft and sulfite processes. A further suitable type of fibers is chemically stiffened cellulose, i.e., stiffened by chemical means to increase the stiffness of the fibers under both dry and aqueous conditions. Such means can include the addition of a chemical stiffening agent that, for example, coats and/or impregnates the fibers or by stiffening of the fibers by altering the chemical structure, e.g., by crosslinking polymer chains, as known in the art. Curl may be imparted to the fibers by methods including chemical treatment or mechanical twisting. Curl is typically imparted before crosslinking or stiffening.

Hydrophilic fibers, particularly (optionally modified) cellulosic fibers are typically preferred. However, hydrophilic fibers can also be obtained by hydrophilizing hydrophobic fibers, such as surfactant-treated or silica-treated thermoplastic fibers. Surfactant-treated fibers can be made by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber.

Suitable synthetic fibers can be made from polyvinyl chloride, polyvinyl fluoride, polytetrafluoroethylene, polyvinylidene chloride, polyacrylics, polyvinyl acetate, polyethylvinyl acetate, non-soluble or soluble polyvinyl alcohol, polyolefins such as polyethylene and polypropylene, polyamides such as nylon, polyesters, polyurethanes, polystyrenes, and the like. In some embodiments, the synthetic fibers are thermoplastic, e.g. having a melt point of at least 50° C.-75° C. less and no greater than 190 or 175° C.

Generally the (e.g. thermoplastic) synthetic fibers have an average width, diameter, or cross-section dimension of at least 5, 10, 15, or 20 microns. The average diameter may range up to 1000 microns (1 mm), yet is typically no greater than 800 microns, or 700 microns, or 600 microns, and in some embodiments no greater than 500 microns or 400 microns. In some embodiments, the average diameter of the fibers of the web is no greater than 300, 250, 200, 150, 100, 75 or 50 microns. Smaller diameter staple fiber webs can provide improved flexibility (e.g. a lower work of compression). The filament cross sectional dimension (and shape of the cross section) is preferably substantially, or essentially, uniform along the length of the filament, e.g., uniformly round. The surface of the filament is typically smooth. The fibers can be in the shape or form of fibers, strips, or other narrow and long shapes. Aggregations can be made up of a plurality of fibers with the same or different plastic compositions, geometric shapes, sizes, and/or diameters. The fibers are typically solid. The fibers can be circular or round in cross section or non-circular in cross section, e.g., lobal, elliptical, rectangular, triangular, and shapes with radial arms such as "x-shaped". For embodiments wherein a thermoplastic fiber is formed from melt-extrusion processes (e.g. spunbond or melt blown) the length of the fibers is continuous. The length of the staple fibers (i.e. fibers) is typically at least 1, 2, or 3 cm, and commonly no greater than 15 cm. In some embodiments, the length of the fibers is no greater than 10, 9, 8, or 7 cm.

The fluid storage layer may be a preformed fibrous web. There are a variety of "dry-laid' and "wet-laid" web-making processes described in the art. Various second (e.g. fluid storage) layers and methods of making such have been described in the art. (See for example U.S. Pat. Nos. 4,610,678 and 6,896,669)

In some embodiments, the second (e.g. fluid storage) layer is typically a highly absorbent material that comprises superabsorbent polymer. In some embodiment, the second layer comprises discrete pieces of superabsorbent polymer, such as the previously described discrete pieces of SAP, optionally included in the polymeric foam. The second absorbent layer may be substantially free of superabsorbent fiber or rayon/superabsorbent fiber. The second (e.g. fluid storage) layer may comprise a blend of cellulosic fibers and superabsorbent material. One illustrative second (e.g. fluid storage) layer has a basis weight from about 100 $g/m^2$ to about 700 $g/m^2$ which has been air-laid as a bottom layer of pulp, a middle layer of pulp and superabsorbent polymer disposed in amongst the pulp, and a top layer containing at least some pulp. The second absorbent layer or material may have a density of 0.25 or 0.3 g/cc to about 0.5 g/cc.

The second (e.g. fluid storage) layer typically comprises at least 5 or 10 wt-% and preferably at least 15, 20, 25 or 30 wt-% of superabsorbent polymer. The superabsorbent polymer is typically no greater than 75 wt-% of the second (e.g. fluid storage) layer and in some embodiments, no greater than 55, 50, 45, or 40 wt-%. The second (e.g. fluid storage) layer may have a basis weight of at least 150 to 200 $g/m^2$ and typically no greater than 500 $g/m^2$.

The second absorbent layer can have basis weight less than, equal to, or greater than the (e.g. polyurethane) foam. The average basis weight of the composite may be at least 150, 200, 250, or 300 gsm and typically no greater than 1000 gsm. In some embodiments the average basis weight of the composite is no greater than 900, or 800 gsm, or 600 gsm.

The first absorbent (e.g. fluid transport) layer and second (e.g. fluid storage) layer can be joined together by any suitable technique. In one embodiment, the layers are joined together with an adhesive. Examples of suitable adhesives include emulsion, hot melt, curable, or solvent-based adhesives. Suitable pressure sensitive adhesives include (meth)acrylate-based pressure sensitive adhesives, such as those described in U.S. Pat. No. Re 24,906 (Ulrich), polyurethane adhesives, natural or synthetic rubber-based adhesives, epoxy adhesives, curable adhesives, phenolic adhesives, and the like.

There are various ways in which the first absorbent layer can be utilized (e.g. as a fluid transport element) proximate a second absorbent layer, some of which are depicted in FIGS. 1-4. FIGS. 1-4, depict cross-sectional views of an absorbent article comprising absorbent composite 10 disposed between a fluid pervious topsheet 40 and fluid impervious backsheet 50. The absorbent composite comprises various arrangements of a first absorbent layer 20 and a second absorbent layer 30 in fluid communication with each other. The first absorbent layer comprises a polymeric foam 21.

In some embodiments, such as depicted in FIG. 1 the first absorbent layer 20 comprises a continuous layer of the polymeric foam and the second absorbent layer 30 comprises a continuous layer of a fluid storage material, such as cellulosic fiber and SAP. In this embodiment, the first absorbent layer has about the same cross-sectional width as the second absorbent layer.

Figure 2:
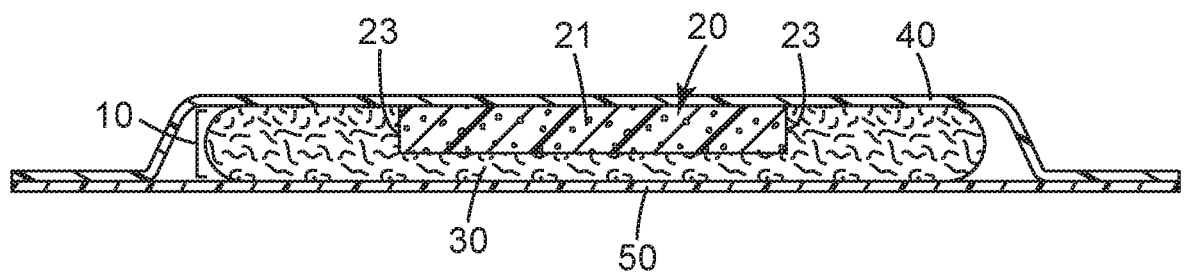

In other embodiments, the cross-sectional width of the first absorbent layer is less than the width of the second absorbent layer. For example, FIG. 2 depicts the polymeric foam 21 inserted within the second absorbent layer 30 such that substantially all the lateral edges 23 (i.e. faces orthogonal to the major surfaces that define the thickness of the polymeric foam) of foam 21 are in fluid communication with the second absorbent layer 30.

Figure 3:
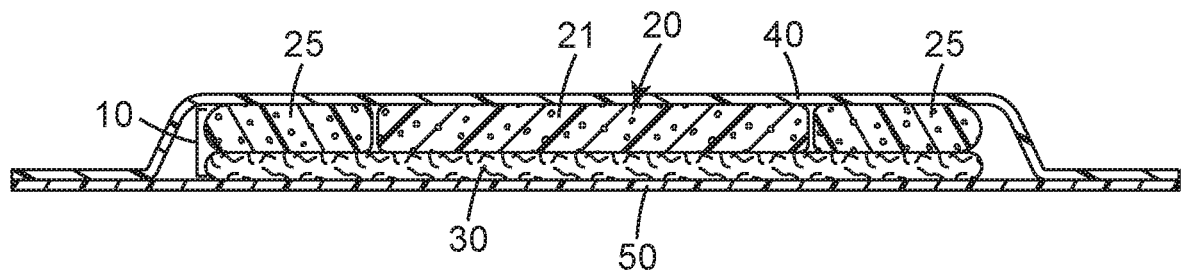

FIG. 3 depicts a multi-component first absorbent layer comprising polymeric foam 21 in a central region 20 and a different fluid transport material 25 disposed on opposing sides of the central region. In one embodiment, fluid transport material 25 may comprise a foam having a different (e.g. higher) SAP content than 20. Alternatively, fluid transport material 25 may comprise a commercially available material used for acquisition layers in disposable absorbent articles such as air bond staple fibers, adhesively bonded staple fibers, and thermally point bonded staple fibers. In yet another embodiment, the central region 20 may comprise a different fluid transport material with the fluid transport material of the opposing sides 25 comprising the polymeric foam as described herein.

Figure 4:
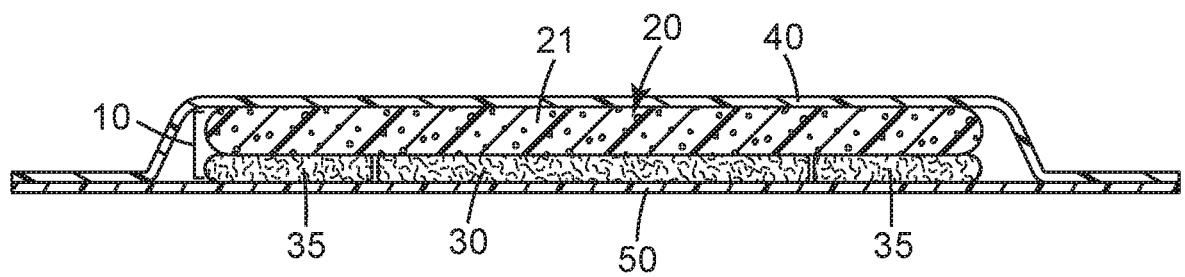

FIG. 4 depicts a multi-component second absorbent layer wherein a SAP containing cellulosic fiber web 30 is present in a central region and a different fluid storage material 35 disposed on opposing sides of the central region. In one embodiment, fluid storage material 35 may comprise an absorbent foam.

In yet other embodiments, (not shown) both the first absorbent layer 20 and the second absorbent layer may both comprise multi-components.

The polymeric (e.g. polyurethane) foam typically has an (e.g. average) absorption rate of less than 60 seconds, 45 seconds, or about 30 seconds and in favored embodiments less than 15 seconds, 10 seconds, 5 seconds, 4 seconds, 3 seconds, or 2 seconds.

The absorbent composite typically has an absorption capacity of at least 10, 11, 12, 13, 14, 15, 16, 17, 18, 19 or 20 g/g. The absorbent composite typically has an absorption capacity of at least 1, 1.1, 1.2, 1.3, 1.4, 1.5, 1.6, 1.7, 1.8, 1.9, 2.0, 2.1, or 2.2 g/cc. The absorption capacity of the absorbent composite is typically no greater than the second layer. The absorbent composite can exhibit a strike through of less than 20, 15, or 10, 9, 8, 7, 6 and in some embodiments less than 5, 4, 3, 2, or 1 second. The composite can exhibit a rewet less than 2 or 1.5. or 1.0 grams. In some embodiments, the rewet is less than 0.9, 0.8, 0.7, and in some embodiments 0.6 or 0.5 or 0.4, or 0.3, or 0.2 grams. The composite can exhibit various combinations of the absorption capacity, strike though, and rewet properties just described. The various numerical values expressed for absorption capacity, strike though, and rewet described herein refer to the average absorption capacity, average strike though, and average rewet unless specified otherwise.

The composite typically has an absorption capacity greater than the polymeric foam. Further, the composite typically has an absorption capacity less than the second absorbent layer. The strike through of the composite is lower (better than) the second absorbent layer. In some embodiments, the strike though is lower than the polymeric foam. Thus, the composite can have a strike though lower than either individual layer. The rewet of the composite is significantly lower (better than) the polymeric foam. In some embodiments, the rewet of the composite is lower than the second absorbent layer. The composite can exhibit good absorption capacity in combination with improved strike through and/or improved rewet.

The absorbent composite of the first (e.g. foam) absorbent layer and the second (e.g. fibrous) absorbent layer can be utilized as an absorbent article, such as suitable for use for spill containment or medical uses, such as wound dressings. In other embodiments, such as a disposable diaper, a feminine hygiene article, or adult incontinence article, the absorbent composite may further comprise another substrate, such as a fluid pervious topsheet and/or a fluid impervious backsheet.

The topsheet 40 is typically the body-facing surface of the absorbent article. Thus, the topsheet comes in contact with a wearer's skin during use of the absorbent article. The topsheet is typically compliant, soft feeling, and non-irritating to the wearer's skin. Further, the topsheet is liquid pervious, permitting liquids to readily penetrate through its thickness. Suitable topsheets may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. The topsheet is typically a hydrophobic material to isolate the wearer's skin from liquids in the absorbent material. Thus, the topsheet is typically a different material than the underlying first absorbent foam layer.

There are a number of manufacturing techniques which may be used to manufacture the topsheet. The topsheet may be woven, non-woven, spunbonded, carded, or the like. An illustrative topsheet is carded, and thermally bonded (1.5 denier polypropylene staple fibers). The topsheet may have a basis weight from about 18 to about 25 grams per square meter. Further, the topsheet typically has a minimum dry tensile strength of at least about 400 grams per centimeter in the machine direction and a wet tensile strength of at least about 55 grams per centimeter in the cross machine direction.

The backsheet 50 is impervious to liquids and typically is a thin plastic film, although other liquid impervious materials may also be used. The backsheet is typically flexible, meaning that it is compliant and will readily conform to the general shape and contours of the wearer's body. The backsheet prevents the exudates absorbed and contained in the absorbent material from wetting articles which contact the absorbent article such as bed sheets and undergarments. One illustrative backsheet is polyethylene film having a thickness of from about 0.012 mm (0.5 mil) to about 0.051 centimeters (2.0 mils). The backsheet may be embossed and or matte finished to provide a more clothlike appearance. Further, the backsheet may permit vapors to escape from the absorbent member while still preventing exudates from passing through the backsheet.

In a typical disposable absorbent article, the topsheet and backsheet are associated together in any suitable manner. Typically, the topsheet and the backsheet are affixed directly to each other at the periphery of the article by an attachment means such as an adhesive or any other attachment means as known in the art.

The disposable absorbent article may comprise a variety of other features as known in the art. For example, when the disposable absorbent article is a feminine hygiene or an adult incontinence napkin (also referred to as a "pad"), the article may further comprise wings or flaps as described for example in U.S. Pat. No. 5,472,437 (3M, Akiyama); U.S. Pat. No. 5,730,739 (P&G, Lavash); and U.S. Pat. No. 5,201,727 (Kao Corp., Nakanishi). Feminine hygiene or adult incontinence napkins also typically comprise a pressure sensitive adhesive on the outer surface of the liquid impervious backsheet for bonding the napkin to an undergarment. Further, when the disposable absorbent article is a disposable diaper, the article may further comprise elasticized leg openings. Disposable diapers also typically comprise a means of attaching the front and rear regions such as by use of adhesive tape or mechanically interlocking hook and loop fasteners.

Test Methods

Density Measurement (g/mL): A sample from the center portion of the foam was cut into cubes with each side nominally measuring 8 cm. Each dimension of the cube was measured with digital calipers, the cubes were weighed. The measured weight was divided by the calculated volume to give the density.

Indentation Force Deflection: The indentation force deflection test (IFD) was conducted based generally on the method in ASTM D3574-08. The dimension of the sample was nominally 80 mm by 80 mm by 80 mm and the top platen was 94 mm in diameter. A contact force sufficient to engage a sheet of copy paper between the foam and the platen was used to mark the initial height of the foam. The IFD was measured at deflections of 25% and 65%.

Cell Size Measurement (micrometers): The average diameter of the cells in a polyurethane foam standard was determined using a fluorescence microscope. The foams were cross-sectioned with a blade (in a direction parallel to the direction of foam rise). A portion of a representative surface of the foam sample was colored with fluorescent orange marker (Bic BRITE liner). The cells in a 8 mm×4 mm section of the foam were each measured. The images were analyzed using ImageJ software. A total of 30-140 cell diameters were measured at random points across the cross-sectioned sample with the mean value being reported. For each cell, the longest dimension was measured. However, holes in cell walls were not measured.

Gel Content: Pieces of wire cloth (316 stainless steel, 120×120 mesh, from McMaster-Carr, Elmhurst, Ill.) were cut to 8 cm×4 cm and folded into cages 3 cm×4 cm using the general method outlined in ASTM D2765-11. A foam sample weighing between 0.18 g and 0.22 g was sealed in the cage, and the cage was submerged in refluxing tetrahydrofuran for 24 hours. The cages were removed and dried under vacuum at 70° C. for four hours. The weight of the sample remaining in the cage was divided by the original weight of the sample to determine the gel content of the foam.

Constant Deflection Compression Set (%): The constant deflection compression set test was conducted in accordance with ASTM D3574-08 for approximately 50% deflection of the initial thickness. The samples were cut with a band saw to dimensions of 50 mm by 50 mm by approximately 25 mm. The metal plates of the test apparatus were secured with the inclusion of a spacer element so that the bottom surface of the upper plate was positioned 12.5 mm from the top surface of the lower plate. The sample was secured in the tightened apparatus and maintained in an oven at 37.8° C. (100° F.) for 22 hours. The resulting compression set values ($C_t$) are reported.

Foam Saline Absorption Rate (seconds): A few drops of 0.9 wt.-% saline solution were added to sheets of foam (8 cm×8 cm, between 3 mm and 7 mm thick). The time required for the solution to visibly be absorbed into the foam was recorded. At least three replicates were performed, each in a unique location. The average value was reported. In some cases, a bimodal performance was observed, and in those cases the average times for both of the general performance regimes are reported.

Absorption Capacity: Saline solution (90 mL of 0.9 wt.-% NaCl in deionized water) was poured into a 100 ml disposable Petri dish. A 10 cm×10 cm sample was weighed and recorded as "dry weight". The sample was immersed into the saline solution and allowed to saturate for 5 minutes. The sample was removed by using tweezers to hold a corner of the sample. The sample was suspended vertically to drip dry for 2 minutes. The wet weight was recorded and the absorption capacity was calculated using the following equation:

$$\text{Absorption Capacity (g/g)} = [(\text{wet sample weight} - \text{dry sample weight})/\text{dry sample weight}]$$

Strike Through Time (sec): The strike through time was measured using the saline solution and a test jig. The jig was made of PLEXIGLASS™ acrylic with the dimensions of 10.16 cm×10.16 cm×2.54 cm (4 inch×4 inch×1 inch). A 2.54 cm hole (1 inch) was cut in the center of the acrylic jig. The test jig weighed about 284 grams. Unless specified otherwise, the test sample was 10 cm×10 cm. The test sample was placed under the test jig and positioned so that the hole in the acrylic was directly above the center of the sample. Saline solution (10 mL of 0.9 wt. % NaCl in deionized water) was poured into the hole and the time (in seconds) required for the saline solution to penetrate into the test sample was recorded. To enhance visualization, the saline solution was dyed with blue food coloring. The test samples were oriented so that the polyurethane foam layer was in direct contact with the acrylic surface of the test jig. In this orientation, the polyurethane foam layer was the first surface of the test sample to come in contact with the saline solution.

Rewet (g): The rewet measurement was determined using the same test jig as described for the strike through time measurement. The test samples were 10 cm×10 cm. The test sample was placed under the test jig and positioned so that the hole in the PLEXIGLAS™ acrylic was directly above the center of the sample. The test samples were oriented so that the polyurethane foam layer was in direct contact with the acrylic surface of the test jig. In this orientation, the polyurethane foam layer was the first surface of the test sample to come in contact with the saline solution. Saline solution (10 mL of 0.9 wt.-% NaCl in deionized water) was poured into the hole and the sample was maintained in the test jig for 5 minutes. The test jig was removed and a stack of ten sheets of FISHERBRAND Q5 90 mm filter paper was placed on top of the test sample. Prior to placement on the sample, the stack of filter paper was weighed to obtain an initial weight. The test jig was reapplied to the sample and a 2 kg gram weight was placed and centered on top of the acrylic test jig providing a 0.51 psi (3.52 kPa) load for 15 seconds. The assembly was removed and the stack of filter paper was weighed again to obtain a final weight. The rewet measurement (in grams) was calculated by subtracting the initial filter paper weight from the final filter paper weight.

Materials

Modified diphenylmethane diisocyanate (MDI) was obtained from Huntsman Chemical Company, The Woodlands, Tex., under the trade designation "SUPRASEC 9634". The "SUPRASEC 9634" material was reported to have the following properties: equivalent weight of 143 g/equivalent, functionality of 2.15, and isocyanate content of 29.3%.

Monomeric diphenylmethane diisocyanate (MDI) containing a high percentage of 2,4-isomer was obtained from Bayer, Leverkusen, Germany, under the designation "MONDUR MLQ".

The first polyether polyol product was obtained from the Carpenter Company, Richmond, Va., under the designation "CARPOL GP1000". The polymer was reported to be prepared from glycerine, and propylene oxide and to have the following properties: average Mn of 1000 g/mol, hydroxyl number of 168, functionality of 3.

The second polyether polyol product was obtained from the Carpenter Company, Richmond, Va., under the designation "CARPOL GP3008". The polymer was reported to be prepared from glycerine, propylene oxide, and ethylene oxide with the ethylene oxide located internally such that the hydroxyl groups are generally all secondary. It was reported to have the following properties: average Mn of 3000 g/mol, hydroxyl number of 56, functionality of 3, ethylene oxide content of 8%.

The third polyether polyol product was obtained from the Carpenter Company, Richmond, Va., under the designation "CARPOL GP4520". The polymer was reported to be prepared from glycerine and propylene oxide and to be capped with ethylene oxide. It was reported to have the following properties: average Mn of 4500 g/mol, hydroxyl number of 36, functionality of 3, and ethylene oxide content of 20%. $^1$H NMR analysis in deuterated DMSO showed a signal from 4.20-4.45 ppm corresponding to the secondary hydroxyl protons, and a signal from 4.45-4.64 ppm corresponding to the primary hydroxyl protons. The ratio of the integrations of the two signals showed 71% primary hydroxyl content and 29% secondary hydroxyl content.

The fourth polyether polyol product was obtained from the Carpenter Company, Richmond, Va., under the designation "CARPOL GP5171". The polymer was reported to be prepared from glycerine and propylene oxide and to be capped with ethylene oxide. It was reported to have the following properties: average Mn of 5000 g/mol, hydroxyl number of 35, functionality of 3, and ethylene oxide content of 71%. $^1$H NMR analysis in deuterated DMSO showed a signal from 4.40-4.46 ppm corresponding to the secondary hydroxyl protons, and a signal from 4.46-4.62 ppm corresponding to the primary hydroxyl protons. The ratio of the integrations of the two signals showed 88% primary hydroxyl content and 12% secondary hydroxyl content.

The solution of triethylene diamine (33 weight percent) in dipropylene glycol was obtained from the Air Products Company, Allentown, Pa., under the trade designation "DABCO 33-LV". The tertiary amine catalyst used to catalyze the urea formation reaction (water with isocyanate) was obtained from the Air Products Company under the trade designation "DABCO BL-17". The trade designated compounds "DABCO DC-198" and DABCO DC-5950" are each silicone glycol copolymer surfactants, obtained from the Air Products Company.

General Foam Polymerization Method: For each sample the components in Table 1 except for the isocyanate were combined in a plastic cup and mixed for 60 seconds at 2000 RPMs with a FLAKTEK mixer. The isocyanate was then added and the sample was mixed for an additional 10 seconds before being poured into a paper cup (15 cm diameter, 12 cm high) that had been treated with Tri-Flow Industrial Lubricant TF20025 as a mold release agent. The cup was placed in a 70° C. oven for 20 minutes to allow the foam to rise and cure.

Determining the Isocyanate Index (Index), % by wt. Ethylene Oxide (EO), % Secondary Hydroxyl (Sec OH), and Average Equivalent Weight of Polyol Component (Avg. Eg. Wt.)

This isocyanate index was calculated by dividing the equivalents of isocyanate by the equivalents of hydroxyl groups and water protons. The ethylene oxide percentage was calculated by dividing the total weight of ethylene oxide in the polyol mixture by the total weight of the foam. The secondary hydroxyl percentage was calculated by first calculating the equivalents (i.e. moles) of secondary hydroxyl groups in the polyol component, dividing that number by the total equivalents of hydroxyl groups excluding water, and multiplying by 100%. The average equivalent weight was calculated by dividing the total weight of the polyol mixture by the total equivalents of hydroxyl groups in the polyol mixture excluding water, catalyst, surfactants or other additives.

Comparative Foams: The polyol mixture from Example 1 of patent application WO2013/180832 had an average hydroxyl equivalent weight of 332 and a secondary hydroxyl content of 51%. That foam had an isocyanate index of 0.80 and an ethylene oxide content of 15.4%. The polyol mixture from Control Example 1 of patent application WO2013/180832 had an average hydroxyl equivalent weight of 332, a secondary hydroxyl content of 51%, an isocyanate index of 1 and an ethylene oxide content of 14.3%. The polyol mixture from Example 3 of patent application WO2013/180832 had an average hydroxyl equivalent weight of 349 and a secondary hydroxyl content of 49%. That foam had an isocyanate index of 0.81 and an ethylene oxide content of 15.8%. The polyol mixture from Example 4 of patent application WO2013/180832 had an average hydroxyl equivalent weight of 331 and a secondary hydroxyl content of 52%. That foam had an isocyanate index of 0.80 and an ethylene oxide content of 17.3%. Those foams had gel contents between 88% and 90%.

The Indentation force deflection (IFD) of Example 1 and Control Example 1 as reported in WO 2013/180832 and the same values reported as a force per area are as follows:

TABLE A

Indentation Force Deflection Test

| Example Number | Force at 25% Deflection (N) | Force per Area at 25% Deflection | Force at 65% Deflection (N) | Force per Area at 65% Deflection |
|---|---|---|---|---|
| Example 1 | 48.6 N | 2.16 kPa | 54.4 N | 2.42 kPa |
| Control Example 1 | 52.0 N | 2.31 kPa | 160.1 N | 7.12 kPa |

Several of these measured properties of the Examples (EX) and Control Examples (CEX) foams were as summarized in Table 2.

TABLE 1

Foam Formulations

| | GP1000 | GP4520 | GP3008 | GP5171 | Water | DC 198 | 33 LV | BL-17 | SUPRASEC 9634 |
|---|---|---|---|---|---|---|---|---|---|
| EX 1 | 7.0% | 8.7% | 19.2% | 23.2% | 1.9% | 0.4% | 0.2% | 0.04% | 39.3% |
| EX 2 | 7.0% | 12.2% | 19.2% | 19.7% | 1.9% | 0.4% | 0.2% | 0.04% | 39.4% |
| CEX 1 | 7.0% | 15.1% | 19.2% | 16.8% | 1.9% | 0.4% | 0.2% | 0.04% | 39.4% |
| EX 3 | | | 27.5% | 33.6% | 1.8% | 0.4% | 0.2% | 0.04% | 36.3% |
| CEX 2 | 9.3% | 26.2% | 2.3% | 20.3% | 1.9% | 0.4% | 0.2% | 0.04% | 39.3% |
| CEX 3 | 5.8% | | 29.0% | 23.2% | 1.9% | 0.4% | 0.2% | 0.04% | 39.4% |
| CEX 4 | 7.0% | 8.7% | 19.2% | 23.3% | 1.9% | 0.06% | 0.2% | 0.04% | 39.5% |
| EX 4 | 7.3% | 9.1% | 20.0% | 24.2% | 2.0% | 0.4% | 0.2% | 0.04% | 36.9% |
| CEX 5 | 7.6% | 9.5% | 20.8% | 25.2% | 2.1% | 0.4% | 0.2% | 0.04% | 34.2% |
| EX 5 | 6.6% | 8.3% | 18.3% | 22.1% | 2.4% | 0.4% | 0.2% | 0.04% | 41.7% |
| CEX 6 | 16.2% | 4.1% | 5.8% | 31.8% | 1.9% | 0.4% | 0.2% | 0.04% | 39.5% |
| EX 6 | 11.1% | 8.2% | 15.2% | 24.0% | 1.9% | 0.4% | 0.2% | 0.04% | 38.8% |
| EX7 | 7.4% | 9.3% | 20.4% | 24.7% | 1.7% | 0.4% | 0.2% | 0.04% | 35.9% |
| EX8 | 6.3% | 7.8% | 17.2% | 20.9% | 2.6% | 0.4% | 0.2% | 0.04% | 44.6% |
| EX 9 | 7.0% | 8.7% | 19.2% | 23.3% | 1.9% | 0.12% | 0.2% | 0.04% | 39.5% |
| EX 10 | 7.0% | 8.7% | 19.2% | 23.2% | 1.9% | 0.4%* | 0.2% | 0.04% | 39.3% |
| CEX. 7** | 7.3% | 9.2% | 20.2% | 24.4% | 2.0% | 0.4% | 0.2% | 0.04% | |

*CD5950 instead of DC198
**further contained 36.2% MONDUR MLQ

TABLE 2

Foam Properties

| | Avg. Eq. Wt | Sec. OH | Index | EO | density (g/cc) | Gel Content | Compression Set | Saline Abs. Rate | Avg. Cell Size (microns) | IFD 25% (kPa) | IFD 65% (kPa) |
|---|---|---|---|---|---|---|---|---|---|---|---|
| EX 1 | 971 | 73% | 1.00 | 19.8% | 0.033 | 97% | 13% | 2, 61 | 440 | 1.1 | 2.8 |
| EX 2 | 967 | 73% | 1.00 | 18.0% | 0.037 | 99% | 14% | 1 | 430 | 1.5 | 4.3 |
| CEX 1 | 964 | 73% | 1.00 | 16.5% | 0.040 | 97% | 13% | 2 | 580 | 1.5 | 4.9 |
| EX 3 | 1282 | 63% | 1.00 | 26.1% | 0.042 | 92% | n.d. | 1 | 500 | 0.33 | 1.4 |
| CEX 2 | 971 | 61% | 1.00 | 19.9% | 0.038 | 100% | 4% | 11 | 530 | 5.9 | 10.1 |
| CEX 3 | 962 | 80% | 1.00 | 18.8% | n.d. | n.d. | n.d. | n.d. | n.d. | n.d. | n.d. |
| CEX 4 | 971 | 73% | 1.00 | 19.8% | 0.046 | 99% | 13% | >300 | 600 | 2.0 | 5.8 |
| EX 4 | 971 | 73% | 0.90 | 20.6% | 0.038 | 94% | 19% | 1 | 450 | 0.59 | 1.8 |
| CEX 5 | 971 | 73% | 0.80 | 19.8% | 0.041 | 81% | n.d. | 1 | 370 | 0.27 | 1.1 |
| EX 5 | 971 | 73% | 0.90 | 18.8% | 0.030 | 97% | 21% | 2 | 420 | 0.92 | 2.7 |
| CEX 6 | 759 | 75% | 0.95 | 23.9% | 0.039 | 99% | 2% | 1 | 860 | 2.0 | 4.3 |
| EX 6 | 855 | 76% | 0.95 | 19.9% | 0.035 | 96% | 11% | 2 | 490 | 1.0 | 2.5 |
| EX 7 | 971 | 73% | 1.00 | 21.0% | 0.047 | 96% | 12% | 2 | 440 | 0.81 | 2.8 |
| EX 8 | 971 | 73% | 0.90 | 17.8% | 0.025 | 98% | n.d. | 1 | 380 | 1.7 | 4.1 |
| EX 9 | 971 | 73% | 1.00 | 19.8% | 0.038 | 99% | 8% | 3, >300 | 480 | 1.4 | 4.0 |
| EX 10 | 971 | 73% | 1.00 | 19.8% | 0.032 | 97% | 17% | 36 | 480 | 0.75 | 2.2 |
| CEX 7 | 971 | 73% | 1.00 | 20.8% | 0.033 | 98% | 9% | 2 | 1210 | 1.0 | 2.2 |

Sec. OH = Secondary Hydroxy
EO = ethylene oxide

The foam in Comparative Example 3 collapsed internally as it polymerized, and it did not produce a foam that was suitable for further testing. All of the foams were generally found to be open cell foams except for Comparative Examples 2, 6, and 8, which were generally closed-cell foams.

Absorbent Composite Preparation and Testing

Selected foams were cut into sheets between 3 mm and 6 mm thick and laminated to a non-woven cellulosic sheet using 3M SPRAY 77 adhesive. These laminates were cut into a square shape 10 cm×10 cm. The resulting laminates were tested for strike through, rewet, and absorption capacity performance. In addition, comparative tests were performed on samples of only the foam or of only the cellulosic sheet. Results were as summarized in Table 3.

TABLE 3

Laminate Properties

|  | Foam | Foam Thickness, mm | Storage Layer Thickness, mm | Strike Through, seconds | Rewet, grams | Absorption Capacity (g/g) |
|---|---|---|---|---|---|---|
| Comp. Example 9 | None | — | 1.20 | 14.3 | 0.05 | 15.27 |
| Comp. Example 10 | Foam Example 1 | 3.9 | None | 5.3 | 8.21 | 5.93 |
| Laminate Example 1 | Foam Example 1 | 3.3 | 1.12 | 1.3 | 0.20 | 9.88 |
| Laminate Example 2 | Foam Example 2 | 4.3 | 1.19 | <1 | 0.34 | 10.69 |
| Laminate Example 3 | Foam Example 5 | 5.1 | 1.25 | 1.1 | 0.38 | 10.5 |
| Laminate Example 4 | Foam Example 7 | 4.5 | 1.16 | <1 | 0.50 | 8.38 |

What is claimed is:

1. An absorbent article comprising:
a first absorbent layer comprising a polymeric foam having an average cell size of at least 100 microns, a density of less than 3 lbs/ft$^3$, and a gel content greater than 90% wherein the polymeric foam comprises superabsorbent polymer pieces distributed therein and has at least one property selected from
   a) an indentation force at 65% deflection of less than 5 kPa;
   b) a constant deflection compression set of less than 25%; and
   c) a combination of a) and b); and
a second absorbent layer in fluid communication with the first absorbent layer.

2. The absorbent article of claim 1 wherein the average cell size of the foam is no greater than 1000 microns.

3. The absorbent article of claim 1 wherein the first absorbent layer is a fluid transport layer and the second absorbent layer has a higher absorption capacity than the first absorbent layer.

4. The absorbent article of claim 1 wherein polymeric foam comprises a polyurethane foam comprising the reaction product of a polymeric polyisocyanate component having an equivalent weight of no greater than 250 g/equivalent; and a polyol component.

5. The absorbent article of claim 4 wherein the polyurethane foam is derived from at least one aromatic polyisocyanate.

6. The absorbent article of claim 4 wherein the polyurethane foam is derived from at least one polymeric polyisocyanate that lacks urethane linkages.

7. The absorbent article of claim 4 wherein the polymeric polyisocyanate is present in an amount ranging from 30 to 45 wt.-% of the total polyurethane.

8. The absorbent article of claim 4 wherein the polyol component has an average equivalent weight ranging from 500 to 2000 g/equivalent.

9. The absorbent article of claim 4 wherein the polyol component comprises an ethylene oxide content ranging from 15-30 wt.-% of the total polyurethane.

10. The absorbent article of claim 9 wherein the ethylene oxide content is greater than 16.5 wt.-%.

11. The absorbent article of claim 1 wherein the polyol component comprises a secondary hydroxyl content of at least 55 mole % and less than 80 mole % of the total hydroxyl content of the polyol component.

12. The absorbent article of claim 11 wherein the secondary hydroxyl content is greater than 61% and less than 80%.

13. The absorbent article of claim 1 wherein the polymeric foam comprises lateral edges in fluid communication with the second absorbent layer.

14. The absorbent article of claim 1 wherein the absorbent article is for use for spill containment, medical uses, wound dressings, disposable diapers, feminine hygiene, or adult incontinence.

15. An absorbent article comprising:
a first absorbent layer comprising a polyurethane foam comprising the reaction product of a polymeric polyisocyanate component having an equivalent weight of no greater than 250 g/equivalent; and
a polyol component wherein the polyol component comprises one or more polyether polyols such that the polyol component comprises
   an average equivalent weight ranging from 500 to 2000 g/equivalent;
   an ethylene oxide content ranging from 15-30 wt.-%;
   a secondary hydroxyl content of at least 55 mole % and less than 80 mole % of the total hydroxyl content of the polyol component; and
   and less than 5 wt-% water; and
a second absorbent layer in fluid communication with the first absorbent layer.

16. The absorbent article of claim 15 wherein the polyurethane foam has an average cell size of at least 100 microns.

17. The absorbent article of claim 15 wherein the polyurethane foam has a density of less than 3 lbs/ft$^3$.

18. The absorbent article of claim 15 wherein the polyurethane foam has a gel content greater than 90%.

19. The absorbent article of claim 15 wherein the polyurethane foam has at least one property selected from
   a) an indentation force at 65% deflection of less than 5 kPa;
   b) a constant deflection compression set of less than 25%; and
   c) a combination of a) and b).

20. The absorbent article of claim 15 wherein the polymeric foam comprises lateral edges in fluid communication with the second absorbent layer.

21. The absorbent article of claim 15 wherein the absorbent article is for use for spill containment, medical uses, wound dressings, disposable diapers, feminine hygiene, or adult incontinence.

22. A polyurethane foam comprising the reaction product of a polymeric polyisocyanate component having an equivalent weight of no greater than 250 g/equivalent; and
a polyol component wherein the polyol component comprises one or more polyether polyols such that the polyol component comprises an average equivalent weight ranging from 500 to 2000 g/equivalent;
an ethylene oxide content ranging from 15-30 wt.-%;
a secondary hydroxyl content of at least 55 mole % and less than 80 mole % of the total hydroxyl content of the polyol component; and
less than 5 wt-% water.

23. The polyurethane foam of claim 22 wherein the polyurethane foam is for use in an absorbent article for spill containment, medical uses, wound dressings, disposable diapers, feminine hygiene, or adult incontinence.

* * * * *

UNITED STATES PATENT AND TRADEMARK OFFICE
CERTIFICATE OF CORRECTION

PATENT NO. : 10,918,537 B2
APPLICATION NO. : 15/760092
DATED : February 16, 2021
INVENTOR(S) : Joe Rule et al.

It is certified that error appears in the above-identified patent and that said Letters Patent is hereby corrected as shown below:

In the Specification

Column 6,
Line 45, delete "dimethylpiperadine," and insert -- dimethylpiperidine, --, therefor.
Lines 45 & 46, delete "methylmorphorine;" and insert -- methylmorpholine; --, therefor.
Lines 47 & 48, delete "hydroxyethylmorphorine;" and insert -- hydroxyethylmorpholine; --, therefor.

Column 14,
Lines 57 & 58, delete "and or" and insert -- and/or --, therefor.

Column 17,
Line 67, delete "FLAKTEK" and insert -- FLACKTEK --, therefor.

In the Claims

Column 21,
Line 59, in Claim 11, delete "claim 1" and insert -- claim 4 --, therefor.

Column 22,
Line 33, in Claim 15, delete "component; and" and insert -- component; --, therefor.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*